(12) United States Patent
Ikushima

(10) Patent No.: US 8,007,723 B2
(45) Date of Patent: Aug. 30, 2011

(54) LIQUID TRANSPORTING DEVICE

(75) Inventor: Kazumasa Ikushima, Mitaka (JP)

(73) Assignee: Musashi Engineering, Inc., Tokyo (JP)

( * ) Notice: Subject to any disclaimer, the term of this patent is extended or adjusted under 35 U.S.C. 154(b) by 550 days.

(21) Appl. No.: 12/279,797

(22) PCT Filed: Feb. 19, 2007

(86) PCT No.: PCT/JP2007/052917
§ 371 (c)(1),
(2), (4) Date: Oct. 20, 2008

(87) PCT Pub. No.: WO2007/097267
PCT Pub. Date: Aug. 30, 2007

(65) Prior Publication Data
US 2010/0229659 A1     Sep. 16, 2010

(30) Foreign Application Priority Data
Feb. 20, 2006   (JP) .................. 2006-043086

(51) Int. Cl.
*G01N 35/10* (2006.01)

(52) U.S. Cl. ............ 422/67; 73/863.01; 73/864.02; 73/864.11; 73/864.25; 422/63

(58) Field of Classification Search .......... 73/863.01, 73/864.02, 864.11, 864.23–864.25, 864.34; 422/63, 67
See application file for complete search history.

(56) References Cited

U.S. PATENT DOCUMENTS
5,770,151 A   6/1998   Roach et al.
7,955,556 B2 *  6/2011   Koike et al. ............. 422/67 X
2004/0100415 A1   5/2004   Veitch et al.

FOREIGN PATENT DOCUMENTS

| JP | 7-120474 A | 5/1995 |
|---|---|---|
| JP | 11-337557 A | 12/1999 |
| JP | 2000-512751 A | 9/2000 |
| JP | 2001-296303 A | 10/2001 |
| JP | 2002-040033 A | 2/2002 |
| JP | 2002-257835 A | 9/2002 |
| JP | 2003-535348 A | 11/2003 |
| JP | 2005-061957 A | 3/2005 |

OTHER PUBLICATIONS

International Search Report of PCT/JP2007/052917, date of mailing May 29, 2007.

* cited by examiner

*Primary Examiner* — Thomas P Noland
(74) *Attorney, Agent, or Firm* — Westerman, Hattori, Daniels & Adrian, LLP

(57) ABSTRACT

A liquid transporting device capable of transporting a liquid, such as dispensing or distributing a liquid, to microplates in number larger than a value mountable on a table. The liquid transporting device comprises a table on an upper surface of which a storing member and a discharge receiving member are detachably mounted, sucking/discharger means, a control unit for transporting a liquid in accordance with a previously incorporate program while relatively moving the sucking/discharger means and the table, an input device, and an alarm signal notifier. The control unit has a function of determining whether ID information of the storing member and/or the discharge receiving member, which is a work target of the previously incorporate program, is identical to ID information of the storing member and/or the discharge receiving member mounted on the table. The control unit continues transporting work when both data of the ID information are identical at the same position, and issues an error signal when different.

19 Claims, 9 Drawing Sheets

[Fig. 1]
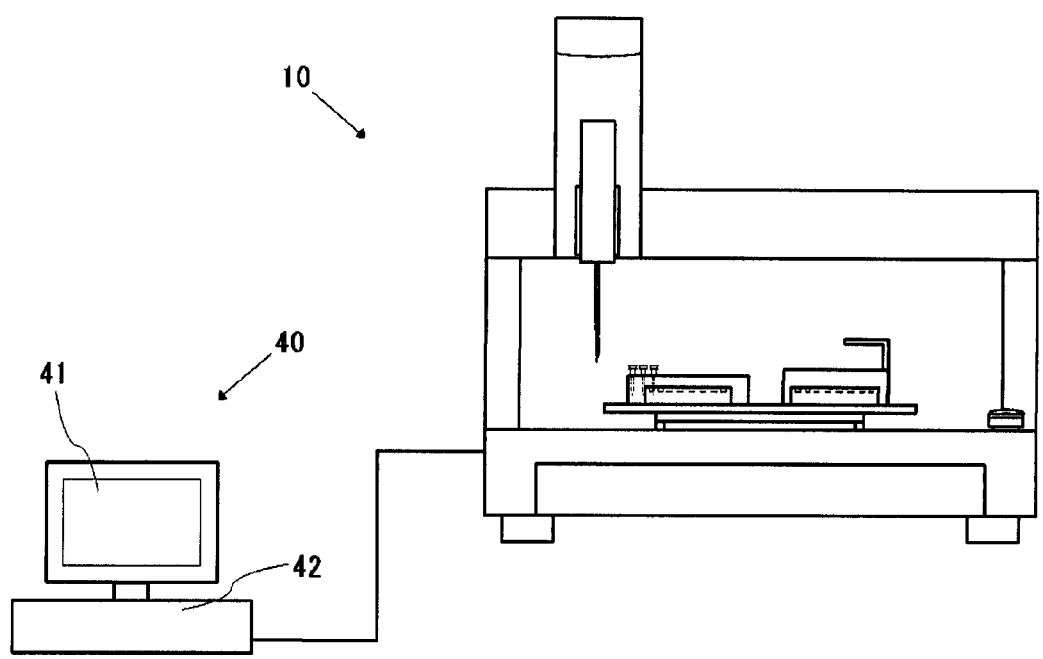

[Fig. 2]
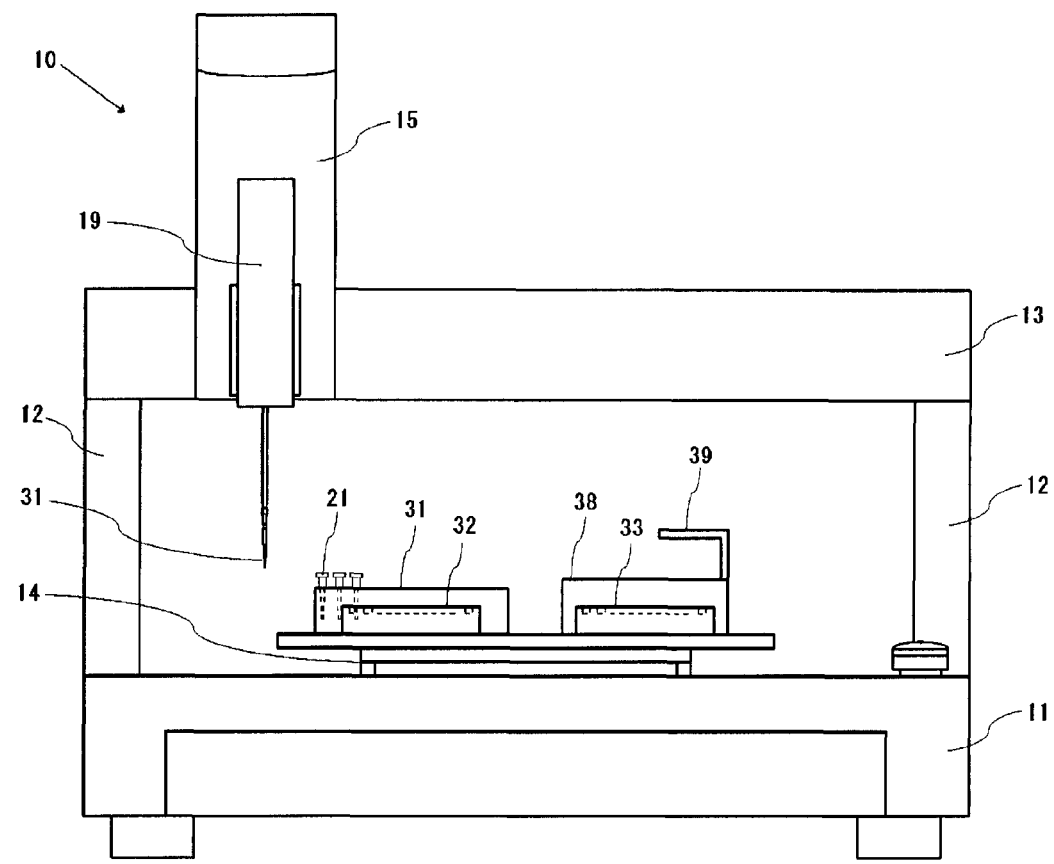

[Fig. 3]
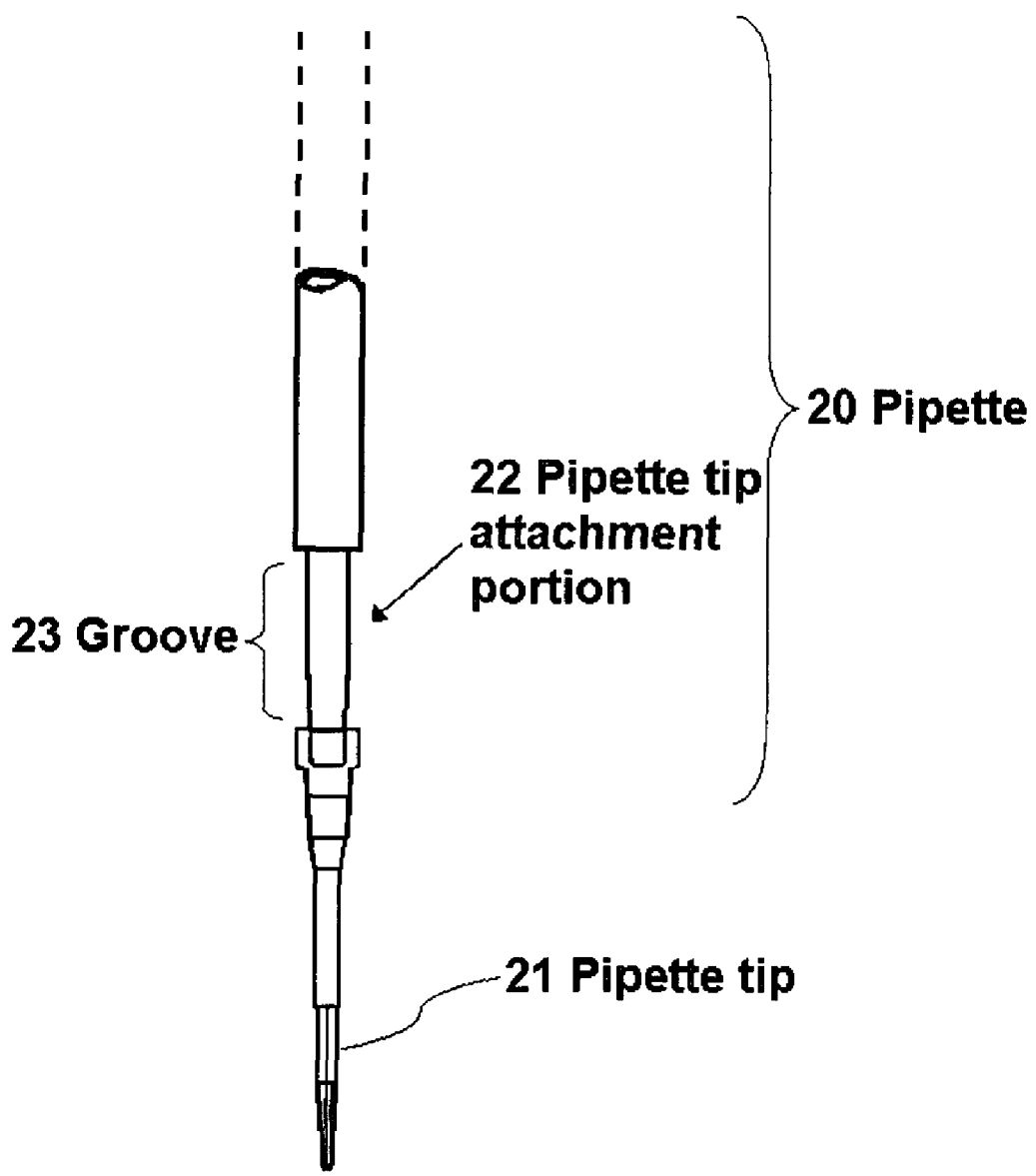

[Fig. 4]
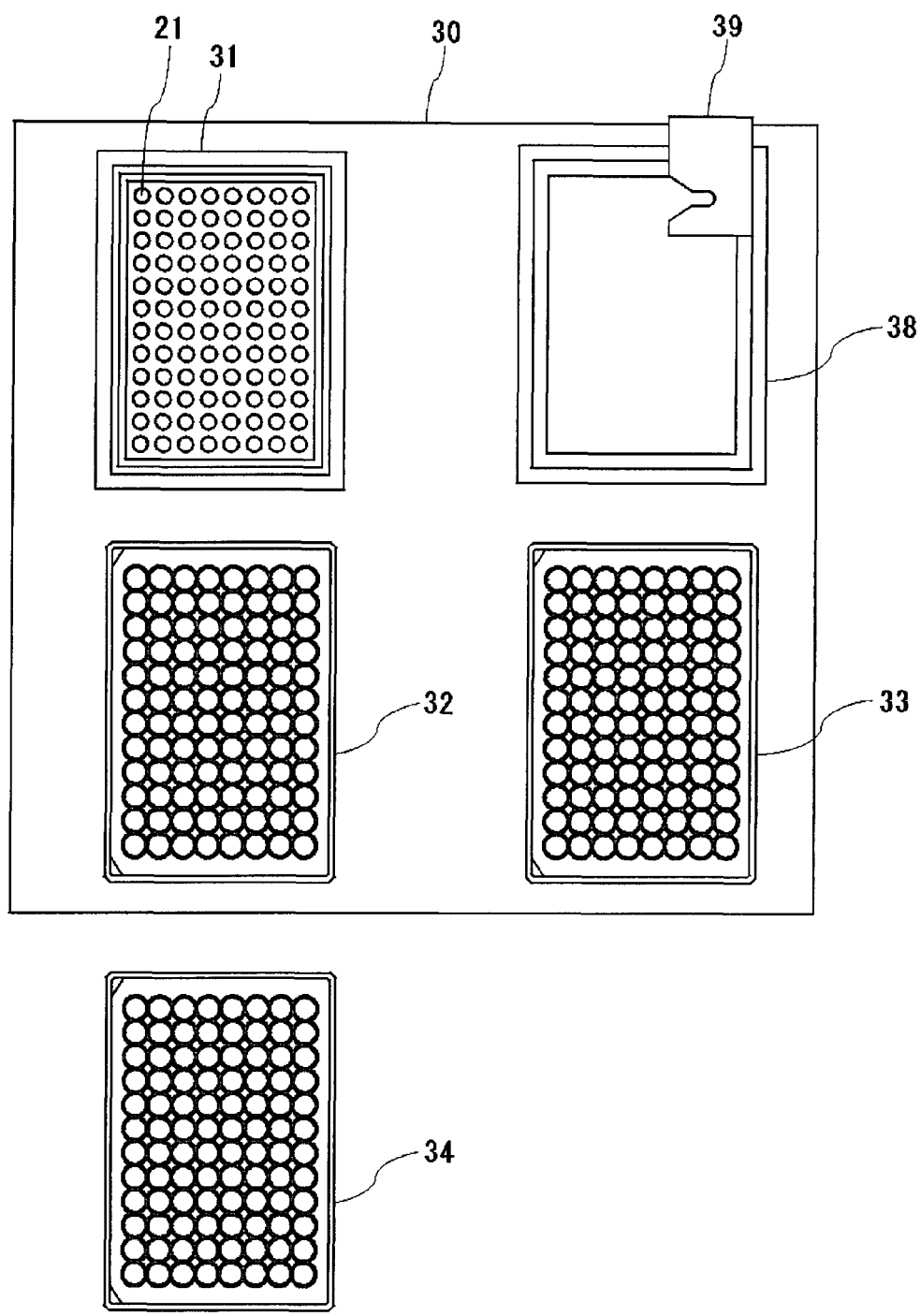

[Fig. 5]
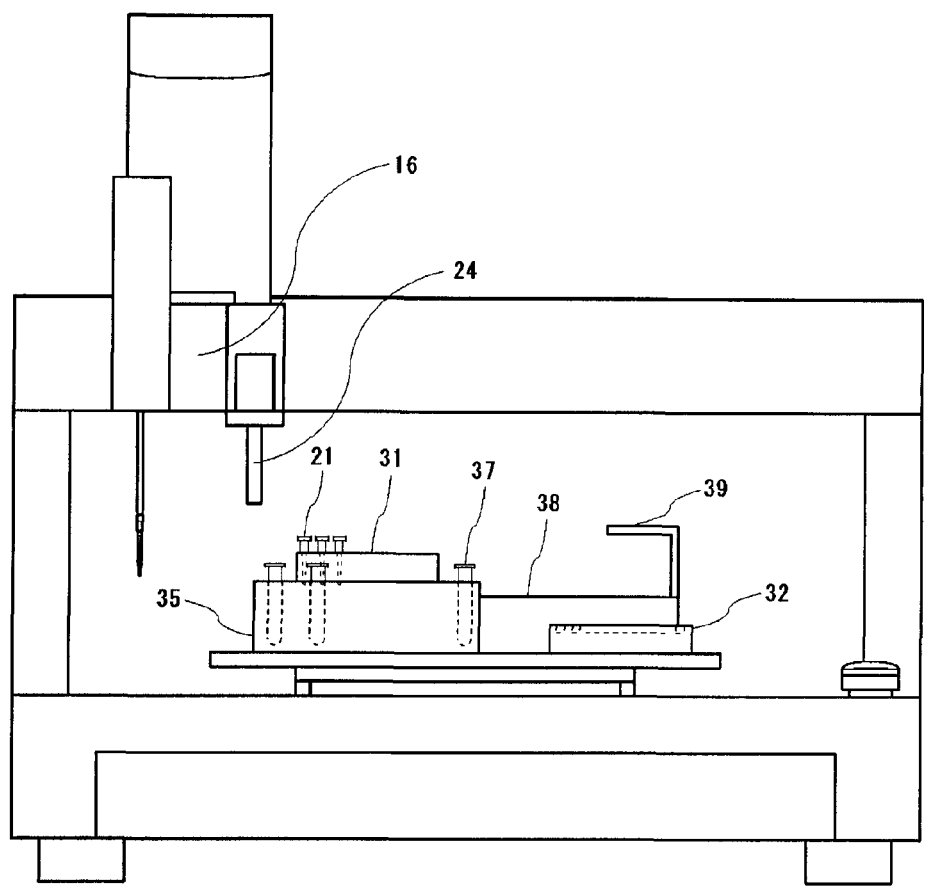

[Fig. 6]
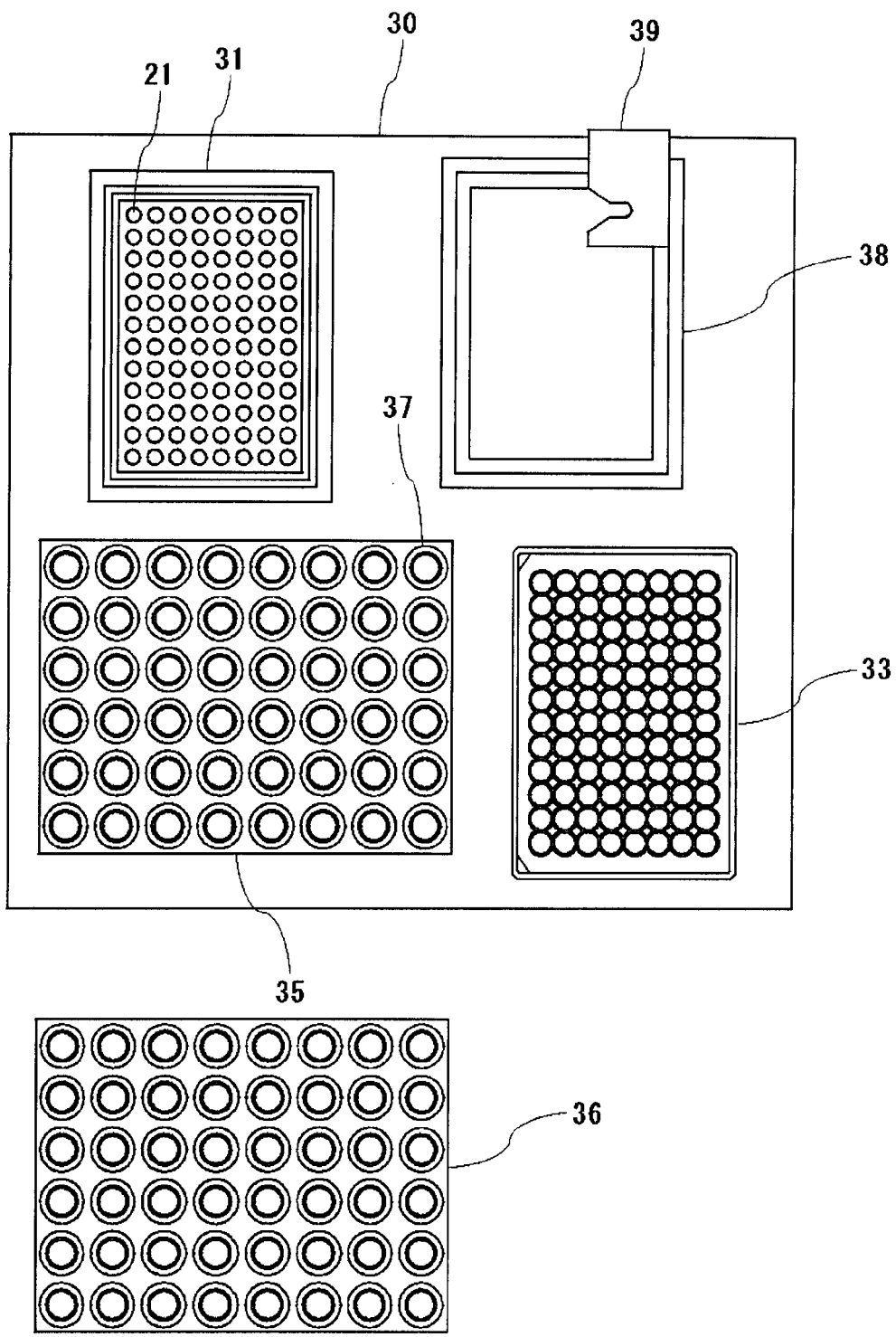

[Fig. 7]
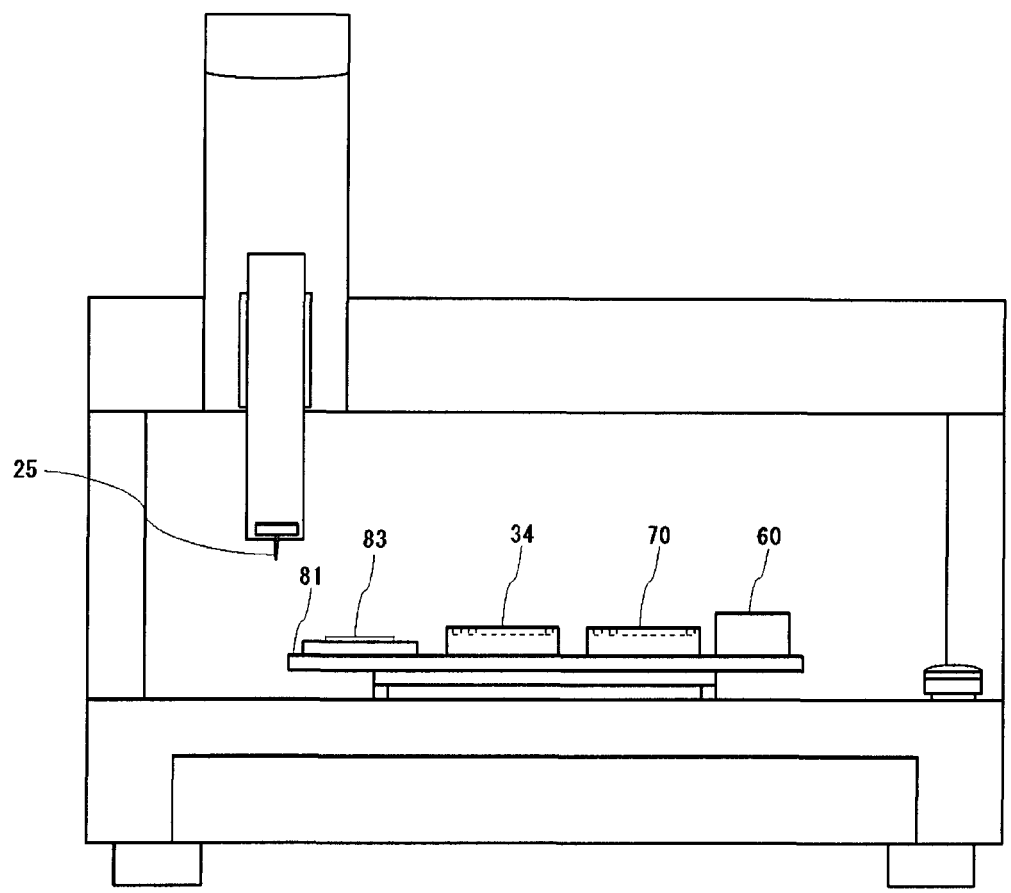

[Fig. 8]
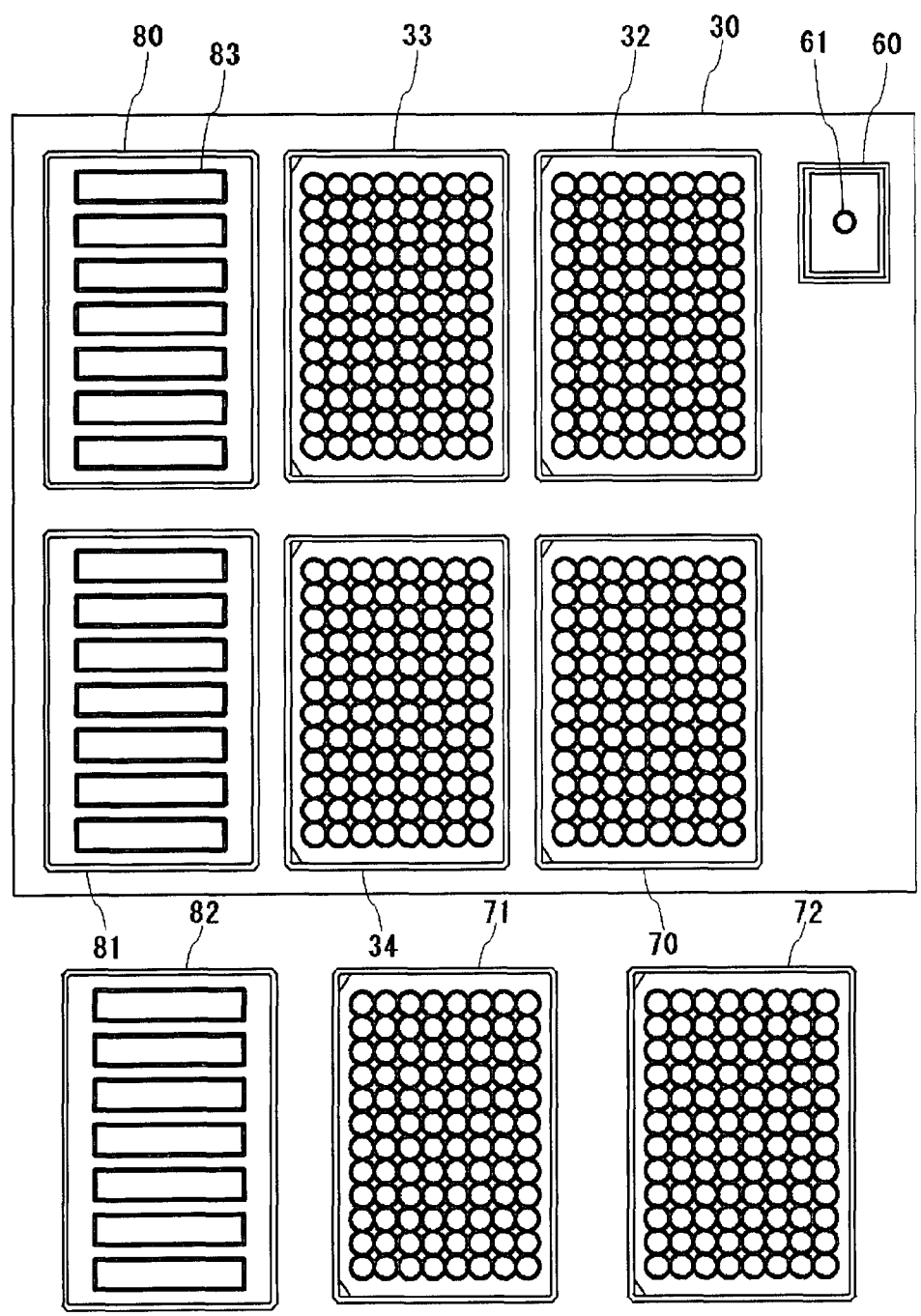

[Fig. 9]
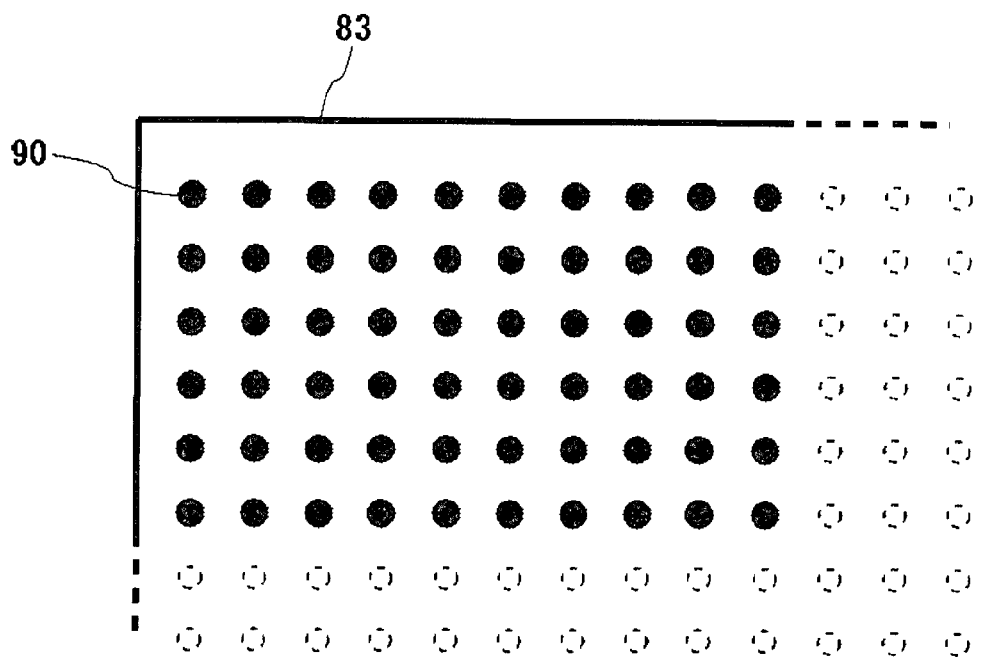
[Fig. 10]
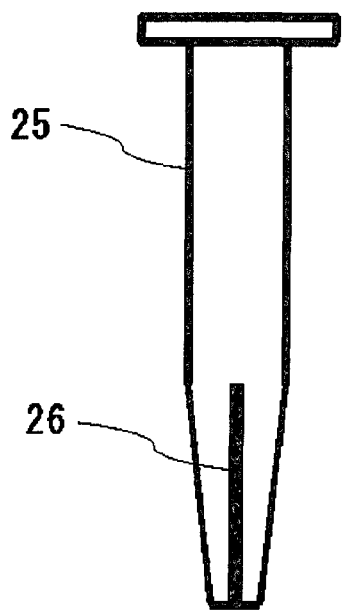

LIQUID TRANSPORTING DEVICE

TECHNICAL FIELD

The present invention relates to a device for dispensing or applying a liquid, including fluids such as water, alcohol, a reagent, protein and a biological sample, to a predetermined storage location or the surface of a plate-like workpiece. More particularly, the present invention relates to a liquid transporting device capable of transporting a liquid, such as dispensing or distributing a liquid, to microplates in number larger than a value mountable on a table.

BACKGROUND ART

In pharmaceutical and biotechnological fields, it is generally performed to systematically evaluate various kinds of processes which are applied to liquid samples, including a biochemical substance, for the purpose of obtaining various kinds of information from the liquid samples.

When evaluating various kinds of processes, plural types of liquid mixtures are used which are prepared by selecting several required ones from among biological samples, solvents, reagents, and other liquid materials, and then mixing the selected materials at a desired proportion.

More specifically, the liquid mixture is prepared by repeating operations of selectively taking out desired amounts of the liquid materials from wells formed in a microplate, called a mother plate, in which various types of liquid materials are stored, and then dispensing the taken-out liquid materials to wells formed in a microplate called a daughter plate.

Because different liquid materials are poured into the wells of the daughter plate from the mother plate, different types of liquid materials are formed in the wells of the daughter plate.

In general, the mother plate is often replaced with a plurality of test tubes.

As a device for performing the above-described dispensing operation, there is, for example, a device developed by the applicant, which is disclosed in Patent Document 1.

Patent Document 1 discloses a substantial liquid material dispensing device for sucking a substantial liquid material from a test tube into a pipette tip attached to a pipette end, and discharging the substantial liquid material into a desired hole formed in a microplate, wherein the dispensing device comprises a head unit having a pipette, a tip case for holding the pipette tip attached to the pipette end, a test tube rack for holding the test tube which stores the substantial liquid material or a liquid material containing the substantial liquid material, and a table unit on an upper surface of which the microplate is placed, the head unit and the table unit being relatively moved to perform dispensing work. According to the embodiment disclosed in Patent Document 1, the basic operation of the substantial liquid material dispensing device is as follows.

(1) The pipette tip is attached to the pipette end by descending the pipette from above the pipette tip held in the tip case.
(2) The pipette is moved into the test tube in which a sample is stored, thereby sucking a desired amount of the sample into the pipette tip.
(3) The pipette is moved toward the desired hole of the microplate, and the sample in the pipette tip is discharged into the desired hole.
(4) The pipette is moved toward a tip release plate in a tip discard box, and the pipette tip is released from the pipette to be dropped into the pipette tip discard box.

The above steps (1) to (4) are repeated until the desired amount of the sample is poured into all the wells of the microplate.

Patent Document 1: Japanese Patent Laid-Open No. 2005-061957

DISCLOSURE OF THE INVENTION

Problems to be Solved by the Invention

As described above, the device disclosed in Patent Document 1 performs the dispensing work in units of the microplate placed on the table.

In the device of that type, however, because the microplate is placed on the table, the number of microplates mountable onto the table is limited depending on an area of the table. Accordingly, when the device has a large size and a large table area is provided, the mother plate and the daughter plate can be each mounted in plural, but such an arrangement is not suitable for reducing the device size. Stated another way, as the device size is reduced, the table area is also required to be reduced correspondingly. In a device having a minimum size, there is a space just enough to accommodate one mother plate and one daughter plate.

Thus, the device size is dominated by the table size, and the table size is dominated by the number of microplates to be mounted on the table. However, when many types of liquid materials are required to prepare the liquid mixtures in the wells of the daughter plate, a plurality of mother plates have to be mounted on the table, and a difficulty is caused in reducing the device size.

The present invention has been made in view of the above-described state of art, and its object is to provide a liquid transporting device capable of transporting a liquid, such as dispensing or distributing a liquid, to microplates in number larger than a value mountable on a table.

Means for Solving the Problems

To solve the above-described problems, the liquid transporting device of the present invention is constituted as follows.

According to a first aspect, the present invention provides a liquid transporting device comprising a table on an upper surface of which are detachably mounted a storing member having a plurality of storage holes to store liquids therein and a discharge receiving member having a plurality of storage holes into which liquids are discharged, sucking/discharging means for sucking and discharging a liquid in a desired amount, a control unit for transporting the liquid from the storing member to the discharge receiving member in accordance with a previously incorporate program while relatively moving the sucking/discharging means and the table, input means for inputting commands to the control unit, and alarm signal notifying means, wherein the control unit has a function of determining whether ID information of the storing member and/or the discharge receiving member, which is a work target of the previously incorporate program, is identical to ID information of the storing member and/or the discharge receiving member mounted on the table, and wherein the control unit continues transporting work when both data of the ID information are identical at the same position, and issues an error signal and notifies the ID information of the storing member and/or the discharge receiving member, which is the work target of the previously incorporate program, through the alarm signal notifying means when the both are different.

According to a second aspect, in the first aspect of the present invention, the alarm notifying means is a monitor for displaying the ID information of the storing member and/or the discharge receiving member, which is the work target of the previously incorporate program, and/or a speaker for producing voices to notify the ID information of the storing member and/or the discharge receiving member, which is the work target of the previously incorporate program.

According to a third aspect, in the first or second aspect of the present invention, when the error signal is issued, the control unit stops the relative movement of the sucking/discharging means and the table.

According to a fourth aspect, in the third aspect of the present invention, when the error signal is issued, the control unit restarts the transporting work after the ID information of the storing member and/or the discharge receiving member, which is the work target of the previously incorporate program, is updated.

According to a fifth aspect, in any one of the first to fourth aspects of the present invention, the storing member and/or the discharge receiving member has a barcode holding the ID information thereof, and the table is provided with a receiver for reading the ID information held by the barcode on the storing member and/or the discharge receiving member which is mounted on the table, and for sending the read ID information to the control unit.

According to a sixth aspect, in any one of the first to fourth aspects of the present invention, the storing member and/or the discharge receiving member has a transmitter circuit electromagnetically holding the ID information thereof, and the table is provided with a receiver for reading the ID information held by the transmitter circuit on the storing member and/or the discharge receiving member which is mounted on the table, and for sending the read ID information to the control unit.

According to a seventh aspect, in any one of the first to sixth aspects of the present invention, the discharge receiving member is a microplate.

According to an eighth aspect, in any one of the first to seventh aspects of the present invention, the storing member is a microplate.

According to a ninth aspect, in any one of the first to seventh aspects of the present invention, the storing member is constituted by a plurality of test tubes supported on a holder.

According to a tenth aspect, in any one of the first to ninth aspects of the present invention, the sucking/discharging means is a pipette.

According to an eleventh aspect, in any one of the first to tenth aspects of the present invention, the sucking/discharging means is a tube or a pin having a slit formed at a distal end thereof, which sucks the liquid by the action of a capillary phenomenon.

EFFECT OF THE INVENTION

With the present invention, since the control unit can issue instructions for storage containers, such as microplates or test tubes, in number larger than a value mountable on the table, the size of a stage can be reduced and hence the overall size of the device can be reduced.

Also, when an instruction is issued for the storage container which is not placed on the stage, the device is stopped and a signal is issued to prompt replacement of the storage container. Therefore, safety in work is ensured.

Further, the program for the liquid transporting work can be designed with no need of considering the number of storage containers serving as liquid supply sources and the number of storage containers serving as liquid supply destinations, which are placed on the stage.

BRIEF DESCRIPTION OF THE DRAWINGS

FIG. 1 is a schematic view showing the overall construction of a liquid transporting device according to a first embodiment of the present invention.

FIG. 2 is an enlarged front view of a device main body shown in FIG. 1.

FIG. 3 is an enlarged front view showing a pipette and a pipette tip in an attached state.

FIG. 4 is an enlarged plan view showing, in an enlarged scale, a table in the device shown in FIG. 1.

FIG. 5 is a front view of a liquid transporting device according to a second embodiment of the present invention.

FIG. 6 is an enlarged front view of a table unit in the device shown in FIG. 5.

FIG. 7 is a front view of a liquid transporting device according to a third embodiment of the present invention.

FIG. 8 is an enlarged front view of a table unit in the device shown in FIG. 7.

FIG. 9 is a schematic view showing a matrix pattern of liquid materials transported to a glass plate.

FIG. 10 is a schematic front view of a pin having a slit.

DESCRIPTION OF REFERENCE CHARACTERS 10 main body
11 base
12 post
13 X-axis moving means
14 Y-axis moving means
15 Z-axis moving means
16 plate
20 pipette
21 pipette tip
22 pipette tip attachment portion
23 groove
24 ultrasonic length measuring device
25 pin
26 slit
30 stage
31 tip case
32 microplate A
33 microplate B
34 microplate C
35 test tube rack A
36 test tube rack B
37 test tube
38 tip discard box
39 tip release plate
40 control unit
41 computer main unit
42 monitor
50 hole
60 cleaning device
61 insertion opening
70 microplate D
71 microplate E
72 microplate F
80 pallet A
81 pallet B
82 pallet C
83 glass plate
90 application point

BEST MODE FOR CARRYING OUT THE INVENTION

The present invention will be described in more detail by referring to embodiments illustrated below, but the present invention is in no way restricted by the following embodiments.

Embodiment 1

Embodiment 1 will be described in connection with the case of preparing various types of liquid mixtures in a daughter plate based on plural types of liquid materials stored in a mother plate.

FIG. 1 is a schematic view showing the overall construction of a liquid transporting device according to an embodiment of the present invention, FIG. 2 is an enlarged front view of a device main body shown in FIG. 1, FIG. 3 is an enlarged front view showing a pipette and a pipette tip in an attached state, and FIG. 4 is an enlarged plan view showing, in an enlarged scale, a table in the device shown in FIG. 1.

<<Construction>>

The liquid transporting device comprises a main body 10 and a control unit 40.

The main body 10 includes a base 11, two posts 12 extending upward from the base 11, an X-axis moving means 13 supported by the posts 12, a Z-axis moving means 15 disposed on the X-axis moving means 13, and a Y-axis moving means 14 disposed on an upper surface of the base 11. The Z-axis moving means 15 is provided with a pipette 20 having a pipette tip attachment portion 22 at a distal end thereof.

A stage 30 is disposed on the Y-axis moving means 14. A microplate A 32, a microplate B 33, a tip case 31, and a tip discard box 38 are detachably mounted to an upper surface of the stage 30.

In this embodiment, the microplate A 32 and a microplate C 34 are used as mother plates, and the microplate B 33 is used as the daughter plate. In FIG. 4, reference character 32 denotes the mother plate that is currently a work target, and 34 denotes the mother plate that becomes a work target next.

Each microplate is constructed such that a plurality of holes are formed in a flat plate in a grid pattern. The holes are called wells.

The tip case 31 is a box-like member having an inner space. A plate-like member constituting an upper surface of the tip case 31 has a plurality of holes formed therein in a grid pattern, and pipette tips 21 are loosely inserted in the holes, respectively. The upper surface of the tip case 31 is positioned at such a level that a distal end of each pipette tip 21 does not contact a lower surface of the tip case, and an edge of each of the holes formed in the upper surface supports a peripheral surface of the pipette tip 21.

The tip discard box 38 is a box-like member provided with a tip release plate 39 extending from a side surface of the tip discard box 38. Spent pipette tips are dropped into the tip discard box 38.

The control unit 40 comprises a computer main unit 42 and a monitor 41. A program for procedures of transporting work is previously installed in the control unit 40, and the liquid transporting device is operated in accordance with the installed program. The procedures of transporting work include information regarding the serial number of the mother plate in which liquid materials to be transported are stored, well positions in each microplate where the liquid materials are stored, amounts of the liquid materials dispensed, the serial number of the microplate used as the daughter plate, and well positions in the daughter plate where the liquid materials are dispensed.

The mother plate and/or the daughter plate may include an identification mechanism (e.g., a barcode or a transmitter circuit such as an IC tag) which holds identification (ID) information, and a receiver may be provided to read the ID information held in the identification mechanism disposed on the mother plate and/or the daughter plate, which is mounted onto the stage 30, and for sending the read ID information to the control unit 40.

Such an arrangement can make a user free from the necessity of manually inputting the ID information of the mother plate and/or the daughter plate, which is mounted onto the stage 30, through an input means (not shown).

<<Operation>>

The liquid dispensing device thus constructed repeatedly performs work of dispensing, from wells of the microplate A 32 and the microplate C 34 in which required liquid materials are stored, those liquid materials into a desired well of the microplate B 33. In other words, a plurality of liquid materials are dispensed from the microplate A 32 and/or the microplate C 34 into one well of the microplate B 33 and are mixed therein to provide a liquid mixture in that well.

Prior to start of the dispensing work, the user selects one of a plurality of dispensing programs, which have been prepared in advance, through the input means (not shown), and inputs the microplate serial numbers corresponding to the mother plate and the daughter plate, which are to be initially mounted onto the stage 30.

The dispensing program prescribes the sequence of the microplates to be mounted on the table and the procedures of the dispensing work. The procedures of the dispensing work include, by way of example, (1) the case in which, after the dispensing work for one well of the microplate B 33 serving as the daughter plate has been completed, the dispensing work is performed for a next well of the daughter plate, and (2) the case in which, after the dispensing work for the liquid material in one well of the microplate A 32 serving as the mother plate has been completed, the dispensing work is performed for a next well of the mother plate. However, the procedures of the dispensing work are not limited to those cases.

At the start of the dispensing work, the program in the control unit 40 obtains information regarding the serial number of the mother plate which becomes a target of the dispensing work, the well position on the microplate where the liquid material is stored, the amount of the liquid material dispensed, and the well position on the daughter plate where the liquid material is dispensed. Of those information items, it is checked whether the serial number of the mother plate as the target of the dispensing work is matched with the serial number of the mother plate mounted on the stage.

After checking whether the input serial number of the mother plate is matched with the serial number of the mother plate mounted on the stage, the dispensing work is started when both the serial numbers are identical to each other.

When both the serial numbers differ from each other as a result of the matching check, i.e., when the appropriate mother plate is not mounted on the stage, the dispensing work is not started and an alarm message for prompting replacement of the microplate is displayed on the monitor 41 (a voice alarm or an indicator lamp may also be used instead). In that case, the dispensing work can be started by the user manually mounting the appropriate mother plate on the table and inputting, through the input means (not shown), a command (recovery command) notifying that the appropriate mother plate has been mounted on the table. When the mother plate includes the above-described identification mechanism, the device can automatically issue the recovery command upon the user just mounting the appropriate mother plate.

The control unit 40 operates the X-axis moving means 13 and the Y-axis moving means 14 to move the pipette 20 to a position above the pipette tip 21 which is contained in the tip case 31, and then operates the Z-axis moving means 15 to move the pipette 20 downward to such an extent that the pipette tip 21 is attached to the distal end of the pipette 20. Thereafter, the Z-axis moving means 15 is operated to move the pipette 20 upward, and the X-axis moving means 13 and the Y-axis moving means 14 are operated to move the pipette tip 21 to a position above the desired well of the microplate A 32. Then, the Z-axis moving means 15 is operated to move the pipette 20 downward to such an extent that the distal end of the pipette tip 21 is dipped into the liquid material stored in the aforesaid desired well. In such a state, the pipette 20 is operated to suck the desired amount of the liquid material into the pipette tip 21.

Next, the Z-axis moving means 15 is operated to move the pipette 20 upward, and the X-axis moving means 13 and the Y-axis moving means 14 are operated to move the pipette 20 to a position above the desired well of the microplate B 33. Then, the Z-axis moving means 15 is operated to move the pipette 21 downward to such an extent that the distal end of the pipette tip 21 enters the aforesaid desired well. In such a state, the pipette 20 is operated to discharge, into that well, the liquid material sucked in the pipette tip 21.

Subsequently, the Z-axis moving means 15 is operated to move the pipette 20 upward, and the X-axis moving means 13 and the Y-axis moving means 14 are operated to move the pipette 20 toward the tip release plate 39 of the tip discard box 38.

As shown in FIG. 3, the pipette 20 has the pipette tip attachment portion 22 which is formed at its distal end and has a smaller diameter than that of a body of the pipette 20. A length of the pipette tip attachment portion 22 is set such that, in a state of the pipette tip 21 being attached, a groove 23 is formed between an upper end of the pipette tip attachment portion 22 and a top edge of the pipette tip 21.

After operating the Z-axis moving means 15 to align the groove 23 and a pipette guide groove of the pipette release plate 39 with each other in height, the X-axis moving means 13 and the Y-axis moving means 14 are operated to horizontally move the pipette 20 such that the groove 23 is positioned in the pipette guide groove of the pipette release plate 39.

Thereafter, when the Z-axis moving means 15 is operated to move the pipette 20 upward, the top edge of the pipette tip 21 comes into contact with a lower surface of the pipette release plate 39. With further upward movement of the pipette 20, the pipette tip 21 is completely released from the pipette 20 and is dropped into the tip discard box 38.

With a series of above-described operations, one of the liquid materials stored in the wells of the microplate A 32 is transported to the microplate B 33 and a first step of the dispensing work is completed.

After completion of the first step of the dispensing work, the control unit proceeds to a second step of dispensing the next liquid material from the mother plate onto the daughter plate.

In the second and subsequent steps, the dispensing work is repeated in the same manner as that in the first step.

More specifically, as in the first step, the program in the control unit 40 obtains information regarding the serial number of the mother plate which becomes a target of the dispensing work, the well position on the microplate where the liquid material is stored, the amount of the liquid material dispensed, and the well position on the daughter plate where the liquid material is dispensed. Of those information items, it is checked whether the serial number of the mother plate as the target of the dispensing work is matched with the serial number of the mother plate mounted on the stage. Depending on the result of the matching check, a recovery operation is also performed, if necessary, as in the first step.

At the end of a final step, as a result of repeating the above-described operations on the microplate B, various types of desired liquid mixtures are stored in all those ones of the wells in the microplate B 33 which are usable to prepare the liquid mixtures.

The matching check made by the control unit 40 is not limited to a combination of the mother plate as the work target and the mother plate actually mounted on the table, it may also performed on a combination of the daughter plate as the work target and the daughter plate actually mounted on the table. Which one of the matching checks should be performed can be optimally selected depending on the type of the program executed. The matching check may be performed on any one of the mother plate and the daughter plate, or on both the plates.

Embodiment 2

In this Embodiment 2, the microplate used as the mother plate in Embodiment 1 is constituted by arranging test tubes in a test tube rack which can hold a plurality of test tubes in a grid pattern. The microplate A 32 in Embodiment 1 is replaced with a test tube rack A 35 holding test tubes, and the microplate C 34 in Embodiment 1 is also replaced with a test tube rack 36 holding test tubes.

FIG. 5 is a front view of a liquid transporting device according to a second embodiment of the present invention, and FIG. 6 is an enlarged front view of a table unit in the device shown in FIG. 5.

In FIGS. 5 and 6, the test tube rack B 36 is not placed on the stage 30 similarly to the microplate C 34 in Embodiment 1. However, as in Embodiment 1, the liquid material not present on the stage 30 can also be dispensed into the microplate B 33, i.e., the daughter plate, by issuing an alarm message from the device, as required.

In transporting work in this Embodiment, a program in the control unit 40 obtains information regarding the serial number of a test tube in which the liquid material to be transferred is stored, the serial number of a rack to which the test tube belongs, the amount through which the liquid material is transferred, the serial number of the microplate which serves as the daughter plate, and the well position on the microplate where the liquid material is discharged.

Further, in the device of this embodiment, the Z-axis moving means 15 is provided with a plate 16, and an ultrasonic length measuring device 24 is disposed on the plate 16 along with the pipette 20.

The test tube can store the liquid material at a height exceeding the overall length of the pipette tip 21. Prior to sucking the liquid material stored in a test tube 37 by the pipette, it is preferable, by the ultrasonic length measuring device 24, to detect the position of a liquid surface in the test tube 37 and to measure the distance up to the position of the liquid surface in order to obtain the distance of movement of the Z-axis moving means 15, which allows the pipette tip 21 at the distal end of the pipette 20 to enter the test tube 37 in an appropriate amount.

Embodiment 3

This Embodiment 3 is related to work for transporting the liquid material, which is stored in the mother plate, to be distributed in a dot grid pattern on a flat glass plate. This embodiment can be applied to, for example, fabrication of a biochip.

FIG. 7 is a front view of a liquid transporting device according to a third embodiment of the present invention, FIG. 8 is an enlarged front view of a table unit in the device shown in FIG. 7, FIG. 9 is a schematic view showing a matrix pattern of liquid materials transported to a glass plate, and FIG. 10 is a schematic front view of a pin having a slit.

This embodiment represents one modified form of the daughter plate storing the liquid mixtures prepared in Embodiments 1 and 2. In other words, the mother plate in this Embodiment 3 can be used as the daughter plate storing the liquid mixtures prepared in Embodiments 1 and 2.

A plurality of flat glass plates 83 are arranged in parallel on each of pallets 80 to 82 which are known per se.

Instead of the pipette in Embodiments 1 and 2, this Embodiment 3 employs a pin 25 having a slit 26 which is formed at a distal end of the pin 25 and which sucks the liquid material by the action of a capillary phenomenon. By contacting the pin 25 with the glass plate 83, the liquid material can be transported onto the glass plate.

The stage 30 is provided with a cleaning device 60 for cleaning the pin 25. The cleaning device 60 is filled with a cleaning liquid and includes an ultrasonic vibrator disposed therein. The cleaning liquid is supplied to the cleaning device 60 through a cleaning liquid supply pipe (not shown) and is discharged through a cleaning liquid drain pipe (not shown). In a state where the pin 25 is inserted into the cleaning device 60 through an insertion opening 61 and a liquid contact portion of the pin 25 is dipped in the cleaning liquid, the pin 25 is cleaned by applying ultrasonic vibrations such that the cleaning liquid is caused to flow from the cleaning liquid supply pipe into the cleaning liquid drain pipe.

The control unit 40 comprises the computer main unit 42 and the monitor 41. A program for procedures of transporting work is previously installed in the control unit 40, and the liquid transporting device is operated in accordance with the installed program. In the transporting work of this Embodiment 3, the program in the control unit 40 obtains information regarding the serial number of the microplate serving as the mother plate in which the liquid material to be transported is stored, the well position on the microplate where the liquid material is stored, the serial number of the glass plate, the serial number of the pallet to which the glass plate belongs, and the position on the glass plate to which the liquid material is transported.

The dispensing work is performed in the same manner as that in Embodiments 1 and 2. Initially, the program in the control unit 40 checks whether the serial number of the mother plate and the serial number of the pallet as the work target is matched with the serial number of the mother plate and/or the serial number of the pallet mounted on the stage.

Depending on the result of checking whether the former serial number of the mother plate and/or serial number of the pallet is matched with the serial number of the mother plate and/or the serial number of the pallet mounted on the stage, the dispensing work is started when both the serial numbers are identical to each other.

When both the serial numbers differ from each other, i.e., when any of the mother plate and the pallet as the work target is not mounted on the stage, the dispensing work is not started and an alarm message is displayed on the monitor 41. More specifically, a message is displayed on the monitor 41 to indicate the serial number of the mother plate and/or the serial number of the pallet mounted on the stage 30 and the serial number of the mother plate and/or the serial number of the pallet to be mounted on the stage 30, and to prompt replacement of the mother plate and/or the pallet on the stage.

When the replacement of the mother plate and/or pallet is required, the user manually mounts the appropriate mother plate and/or pallet on the table and inputs, through the input means (not shown), a command (recovery command) notifying that the appropriate mother plate and/or pallet has been mounted on the table.

In this embodiment, the microplate A 32, the microplate B 33, the microplate C 34, the microplate D 70, the pallet A 80, and the pallet B 81 are arranged on the stage 30.

The X-axis moving means 13 and the Y-axis moving means 14 are operated to move the pin 25 to a position above the well of the microplate, which is selectively instructed from among the microplate A 32, the microplate B 33, the microplate C 34, the microplate D 70. The pin 25 is then moved downward to such an extent that the distal end of the pin 25 is dipped into the liquid material stored in the aforesaid well and the liquid material is sucked into the slit 26. Thereafter, the pin 25 is moved upward.

Next, the X-axis moving means 13 and the Y-axis moving means 14 are operated to move the pin 25 to a position above a transport target location on the glass plate, which is selectively instructed by the program from among the glass plates placed on the pallet A 80 or the pallet B 81. Then, the Z-axis moving means 15 is operated to bring the pin 25 into contact with the aforesaid glass plate. Thereafter, the pin 25 is moved upward again by the Z-axis moving means 15.

Further, the X-axis moving means 13, the Y-axis moving means 14, and the Z-axis moving means 15 are operated such that the pin 25 is inserted into the cleaning device 60 through the insertion opening 61 thereof. In such a state, the cleaning device 60 is operated to clean the pin 25. After the cleaning, the pin 25 is withdrawn through the insertion opening 61.

With a series of above-described operations, the liquid material stored in the mother plate is transported onto the glass plate and a first step of the transporting work is completed.

After completion of the first step of the transporting work, as in the first and second embodiments, the control unit proceeds to a second step of transporting the next liquid material from the mother plate to another desired position on the plate member.

At the end of a final step, a dot matrix of the transported liquid material is formed on each glass plate held on the pallet A 80, the pallet B 81, and the pallet C 82. Dots in the thus-formed dot matrix can be made of different types of the liquid materials.

The above-described transporting work can be performed by progressing steps such that, after completely forming a dot matrix to be prepared on one glass plate, another dot matrix is formed on a next glass plate, or such that, after transporting a liquid material stored in one well of the microplate A 32, serving as the mother plate, onto all those glass plates onto which the liquid material is to be transferred, another liquid material stored in a next well is similarly transported onto all those glass plates onto which the liquid material is to be transferred. As a matter of course, the transporting procedures are not limited to the above-described ones.

As described above, in this embodiment, when the glass plate 83 as the destination of the transported liquid material is not mounted on the stage 30, i.e., when there is a pallet not mounted on the stage 30, the glass plate 83 or the pallet can be handled in a similar manner to the case of the mother plate. However, the daughter plates in Embodiments 1 and 2 can also be replaced during the work as in this Embodiment 3.

The invention claimed is:

1. A liquid transporting device comprising a table on an upper surface of which are detachably mounted a storing member having a plurality of storage holes to store liquids therein and a discharge receiving member having a plurality of storage holes into which liquids are discharged, a sucking/ discharging mechanism for sucking and discharging a liquid in a desired amount, a control unit for transporting the liquid from the storing member to the discharge receiving member in accordance with a previously incorporated program while relatively moving the sucking/discharging mechanism and the table, an input device for inputting commands to the control unit, and an alarm signal notifying device, the liquid transporting device enabling work to be performed on the storing member outside the table and/or the discharge receiving member outside the table, wherein the control unit stores, as first ID information, ID information of the storing member and/or the discharge receiving member, which is a work target of the previously incorporated program, stores, as second ID information, ID information of the storing member and/or the discharge receiving member mounted on the table, and determines whether the first ID information and the second ID information are identical, when transporting work is performed, wherein the transporting work is executed when both the first ID information and the second ID information are identical, and wherein the alarm signal notifying device issues a signal for prompting replacement of the storing member and/or the discharge receiving member mounted on the table and notifies the ID information of the storing member and/or the discharge receiving member outside the table, which is the work target of the previously incorporated program, when both are different.

2. The liquid transporting device according to claim 1, wherein the alarm notifying device is a monitor for displaying the ID information of the storing member and/or the discharge receiving member, which is the work target of the previously incorporated program, and/or a speaker for producing voices to notify the ID information of the storing member and/or the discharge receiving member, which is the work target of the previously incorporated program.

3. The liquid transporting device according to claim 1, wherein when the signal for prompting the replacement is issued, the control unit stops the relative movement of the sucking/discharging mechanism and the table.

4. The liquid transporting device according to claim 3, wherein when the signal for prompting the replacement is issued, the control unit restarts the transporting work after the ID information of the storing member and/or the discharge receiving member, which is the work target of the previously incorporated program, is updated.

5. The liquid transporting device to claim 4, wherein the alarm notifying device is a monitor for displaying the ID information of the storing member and/or the discharge receiving member, which is the work target of the previously incorporated program, and/or a speaker for producing voices to notify the ID information of the storing member and/or the discharge receiving member, which is the work target of the previously incorporated program.

6. The liquid transporting device to claim 4, wherein the storing member and/or the discharge receiving member has a barcode holding the ID information thereof, and wherein the table is provided with a receiver for reading the ID information held by the barcode on the storing member and/or the discharge receiving member which is mounted on the table, and for sending the read ID information to the control unit.

7. The liquid transporting device to claim 4, wherein the storing member and/or the discharge receiving member has a barcode holding the ID information thereof, and wherein the table is provided with a receiver for reading the ID information held by the barcode on the storing member and/or the discharge receiving member which is mounted on the table, and for sending the read ID information to the control unit.

8. The liquid transporting device to claim 4, wherein the discharge receiving member is a microplate.

9. The liquid transporting device to claim 4, wherein the storing member is a microplate.

10. The liquid transporting device to claim 4, wherein the storing member is constituted by a plurality of test tubes supported on a holder.

11. The liquid transporting device to claim 4, wherein the sucking/discharging mechanism is a pipette.

12. The liquid transporting device to claim 4, wherein the sucking/discharging mechanism is a tube or a pin having a slit formed at a distal end thereof, which sucks the liquid by the action of a capillary phenomenon.

13. The liquid transporting device according to claim 1, wherein the storing member and/or the discharge receiving member has a barcode holding the ID information thereof, and wherein the table is provided with a receiver for reading the ID information held by the barcode on the storing member and/or the discharge receiving member which is mounted on the table, and for sending the read ID information to the control unit.

14. The liquid transporting device according to claim 1, wherein the storing member and/or the discharge receiving member has a barcode holding the ID information thereof, and wherein the table is provided with a receiver for reading the ID information held by the barcode on the storing member and/or the discharge receiving member which is mounted on the table, and for sending the read ID information to the control unit.

15. The liquid transporting device according to claim 1, wherein the discharge receiving member is a microplate.

16. The liquid transporting device according to claim 1, wherein the storing member is a microplate.

17. The liquid transporting device according to claim 1, wherein the storing member is constituted by a plurality of test tubes supported on a holder.

18. The liquid transporting device according to claim 1, wherein the sucking/discharging mechanism is a pipette.

19. The liquid transporting device according to claim 1, wherein the sucking/discharging mechanism is a tube or a pin having a slit formed at a distal end thereof, which sucks the liquid by the action of a capillary phenomenon.

* * * * *